United States Patent
Kato et al.

(10) Patent No.: US 10,377,984 B2
(45) Date of Patent: Aug. 13, 2019

(54) CELL CULTURE MEDIUM AND CULTURE METHOD USING THE SAME

(71) Applicants: KANEKA CORPORATION, Osaka-shi, Osaka (JP); NATIONAL HOSPITAL ORGANIZATION, Tokyo (JP)

(72) Inventors: Tomohisa Kato, Takasago (JP); Yonehiro Kanemura, Osaka (JP); Tomoko Shofuda, Osaka (JP); Hayato Fukusumi, Osaka (JP)

(73) Assignees: KANEKA CORPORATION, Osaka-Shi, Osaka (JP); NATIONAL HOSPITAL ORGANIZATION, Tokyo (JP)

( * ) Notice: Subject to any disclaimer, the term of this patent is extended or adjusted under 35 U.S.C. 154(b) by 0 days.

(21) Appl. No.: 15/039,747

(22) PCT Filed: Nov. 21, 2014

(86) PCT No.: PCT/JP2014/080904
§ 371 (c)(1),
(2) Date: May 26, 2016

(87) PCT Pub. No.: WO2015/080047
PCT Pub. Date: Jun. 4, 2015

(65) Prior Publication Data
US 2016/0376549 A1 Dec. 29, 2016

(30) Foreign Application Priority Data
Nov. 27, 2013 (JP) .................. 2013-244758

(51) Int. Cl.
*C12N 5/00* (2006.01)
*C12N 5/071* (2010.01)
*C12N 5/074* (2010.01)
*C07K 14/47* (2006.01)

(52) U.S. Cl.
CPC ......... *C12N 5/0037* (2013.01); *C12N 5/0696* (2013.01); *C07K 14/47* (2013.01); *C12N 2500/90* (2013.01); *C12N 2501/998* (2013.01); *C12N 2533/90* (2013.01)

(58) Field of Classification Search
CPC .. C12N 5/0018; C12N 5/0031; C12N 5/0043; C12N 5/005; C12N 5/0603; C12N 5/0606; C12N 5/0696
See application file for complete search history.

(56) References Cited

U.S. PATENT DOCUMENTS 5,721,139 A * 2/1998 Mather ................ C12N 5/0622
435/325

FOREIGN PATENT DOCUMENTS

| JP | 2005-532805 A | 11/2005 |
|---|---|---|
| JP | 2008-92811 A | 4/2008 |
| JP | 2008-92882 A | 4/2008 |
| JP | 2009-501014 A | 1/2009 |
| JP | 2009-77716 A | 4/2009 |
| JP | 2010-148391 A | 7/2010 |
| KR | 10-2010-0130677 A | 12/2010 |
| WO | WO 99/20741 A1 | 4/1999 |
| WO | WO 2014/208295 A1 | 12/2014 |

OTHER PUBLICATIONS

Angelillo-Scherrer et al., "Deficiency or inhibition of Gas6 causes platelet dysfunction and protects mice against thrombosis," Nature Medicine (Feb. 2001), vol. 7, No. 2, pp. 215-221.
Christoph et al., "UNC569, a Novel Small-Molecule Mer Inhibitor with Efficacy against Acute Lymphoblastic Leukemia In Vitro and In Vivo," Mol. Cancer. Res. (Aug. 30, 2013), vol. 12, No. 11, pp. 2367-2377.
Extended European Search Report dated Sep. 15, 2017, in European Patent Application No. 14866554.0.
Holland et al., "R428, a Selective Small Molecule Inhibitor of Axl Kinase Blocks Tumor Spread and Prolongs Survival in Models of Metastatic Breast Cancer," Cancer Res. (Feb. 15, 2010), vol. 70, No. 4, pp. 1544-1554.
Lijnen et al., "Growth Arrest-Specific Protein 6 Receptor Antagonism Impairs Adipocyte Differentiation and Adipose Tissue Development in Mice," Journal of Pharmacology and Experimental Therapeutics (2011), vol. 337, No. 2, pp. 457-464.
Linger et al., "Taking aim at Mer and Axl receptor tyrosine kinases as novel therapeutic targets in solid tumors," Expert Opin. Ther. Targets (2010), vol. 14, No. 10, pp. 1073-1090.
Schroeder, "Discovery of N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS-777607), a selective and orally efficacious inhibitor of the Met kinase superfamily," Journal of Medicinal Chemistry (Mar. 12, 2009), vol. 52, No. 5, pp. 1251-1254.
Schroeder, "Discovery of N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS-777607), . . . ," Journal of Medicinal Chemistry (Mar. 12, 2009), vol. 52, No. 5, pp. S1-S34, XP002773310, Retrieved from the Internet: URL:http://pubs.acs.org/doi/suppl/10.1021/jm801586s/suppl_file/jm801586s_si_001.pdf [retrieved on Aug. 30, 2017] *p. S33.*
Smolock, E. M. and V. A. Korshunov, "Pharmacological inhibition of Axl affects smooth muscle cell functions under oxidative stress," Vascular Pharmacology (2010), vol. 53, pp. 185-192.
Conrad et al., "Generation of pluripotent stem cells from adult human testis," Nature (Nov. 20, 2008), vol. 456, pp. 344-349.

(Continued)

*Primary Examiner* — Allison M Fox
(74) *Attorney, Agent, or Firm* — Birch, Stewart, Kolasch & Birch, LLP

(57) ABSTRACT

It is an object of the present invention to provide a cell culture medium capable of enhancing cell growth efficiency without using feeder cells, in particular which does not comprise serum. The present invention provides a cell culture medium which comprises growth arrest-specific 6 (GAS6) and does not comprise serum.

7 Claims, 9 Drawing Sheets

(56) References Cited

OTHER PUBLICATIONS

Manton et al., "A Chimeric Vitronectin: IGF-I Protein Supports Feeder-Cell-Free and Serum-Free Culture of Human Embryonic Stem Cells," Stem Cells and Development (2010), vol. 19, No. 9, pp. 1297-1305.
Akopian et al., "Comparison of defined culture systems for feeder cell free propagation of human embryonic stem cells," In Vitro Cell. Dev. Biol.—Animal (2010), vol. 46, pp. 247-258.
Bellido-Martin, L. and P. G. de Frutos, "Vitamin K-Dependent Actions of Gas6," Vitamins and Hormones (2008) vol. 78, pp. 185-209.
Chen et al., "Chemically defined conditions for human iPS cell derivation and culture," Nat. Methods (May 2011), vol. 8, No. 5, pp. 424-429.
Cheng et al., "Human Adult Marrow Cells Support Prolonged Expansion of Human Embryonic Stem Cells in Culture," Stem Cells (2003), vol. 21, pp. 131-142.
Chin et al., "Identification of proteins from feeder conditioned medium that support human embryonic stem cells," Journal of Biotechnology (2007), vol. 130, pp. 320-328.
English translation of International Preliminary Report on Patentability and Written Opinion dated Jun. 9, 2016, in PCT International Application No. PCT/JP2014/080904.
Fukusumi, H. and Y. Kanemura, "Development of feeder cells free culture system of human ES/iPS cells," Progress of Medicine (2011), vol. 239, No. 14, pp. 1338-1344.
Hovatta et al., "A culture system using human foreskin fibroblasts as feeder cells allows production of human embryonic stem cells,"Human Reproduction (2003), vol. 18, No. 7, pp. 1404-1409.
Hutchison et al., "SCF, BDNF, and Gas6 are Regulators of Growth Plate Chondrocyte Proliferation and Differentiation," Mol. Endocrinol. (Jan. 2010), vol. 24, No. 1, pp. 193-203.
International Preliminary Report on Patentability and Written Opinion dated May 31, 2016, in PCT International Application No. PCT/JP2014/080904.
International Search Report dated Feb. 24, 2015, in PCT International Application No. PCT/JP2014/080904, with English translation.
Korshunov, V. A., "Axl-dependent signaling: A clinical update," Clin. Sci. (Lond.) (Apr. 2012), vol. 122, No. 8, pp. 361-368.
Loeser et al,. "Human Chondrocyte Expression of Growth-Arrest-Specific Gene 6 and the Tyrosine Kinase Receptor AXL," Arthritis & Rheumatism (Aug. 1997), vol. 40, No. 8, pp. 1455-1465.
Richards et al., "Comparative Evaluation of Various Human Feeders for Prolonged Undifferentiated Growth of Human Embryonic Stem Cells," Stem Cells (2003), vol. 21, pp. 546-556.
Richards et al., "Human feeders support prolonged undifferentiated growth of human inner cell masses and embryonic stem cells," Nature Biotechnology (Sep. 2002), vol. 20, pp. 933-936.
Shamblott et al., "Derivation of pluripotent stem cells from cultured human primordial germ cells," Proc. Natl. Acad. Sci. USA (Nov. 1998), vol. 95, pp. 13726-13731.
Shimoda, J. and T. Hamamoto, "Gas 6 Deficient Mice," Japanese Journal of Thrombosis and Hemostasis (2001), vol. 12, No. 6, pp. 514-521.
Totonchi et al., "Feeder- and serum-free establishment and expansion of human induced pluripotent stem cells," Int. J. Dev. Biol. (2010), vol. 54, pp. 877-886.
Wang et al., "Self-renewal of human embryonic stem cells requires insulin-like growth factor-1 receptor and ERBB2 receptor signaling," Blood (Dec. 1, 2007), vol. 110, No. 12, pp. 4111-4119.
Xiong et al., "Gas6 and the Tyro 3 receptor tyrosine kinase subfamily regulate the phagocytic function of Sertoli cells," Reproduction (2008), vol. 135, pp. 77-87.
Yue et al., "Feeder Cells Support the Culture of Induced Pluripotent Stem Cells Even after Chemical Fixation," PLoS ONE (Mar. 2012), vol. 7, Issue 3, e32707.
Ben-Batalla et al., "Axl, a prognostic and therapeutic target in acute myeloid leukemia mediates paracrine crosstalk of leukemia cells with bone marrow stroma," Blood (Oct. 3, 2013), vol. 122, No. 14, pp. 2443-2452.
Communication Pursuant to Rule 164(1) EPC (Parital Supplementary European Search Report) dated Jun. 21, 2017, in European Patent Application No. 14866554.0.
Gely-Pernot et al., "An Endogenous Vitamin K-Depedent Mechanism Regulates Cell Prolferation in the Brain Subventricular Stem Cell Niche," Stem Cells (2012), vol. 30, pp. 719-731.
Player et al., "Comparisons between Transcriptional Regulation and RNA Expression in Human Embryonic Stem Cell Lines," Stem Cells and Development (2006), vol. 15, pp. 315-323.
Xu et al., "Feeder-free growth of undifferentiated human embryonic stem cells," Nature Biotechnology (Oct. 2001), vol. 19, pp. 971-974.
Japanese Office Action dated Oct. 2, 2018 for corresponding Application No. 2015-550903, along with a English translation.
Chinese Office Action and Search Report, dated Feb. 19, 2019, for Chinese Application No. 201480063892.8, with English machine translations.
Japanese Office Action, dated Mar. 5, 2019, for Japanese Application No. 2015-550903, with an English machine translation.

\* cited by examiner

[Figure 1]
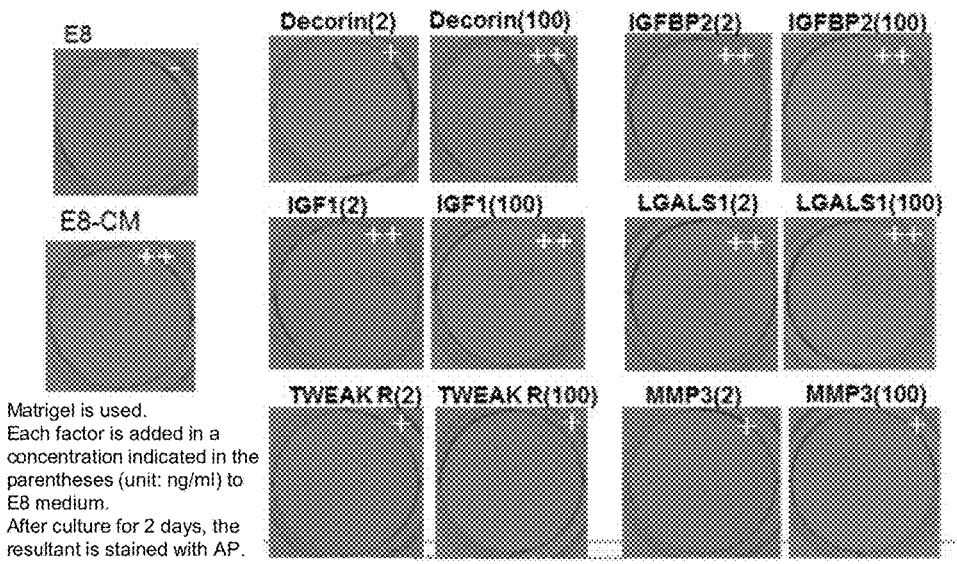
Matrigel is used.
Each factor is added in a
concentration indicated in the
parentheses (unit: ng/ml) to
E8 medium.
After culture for 2 days, the
resultant is stained with AP.
[Figure 2]
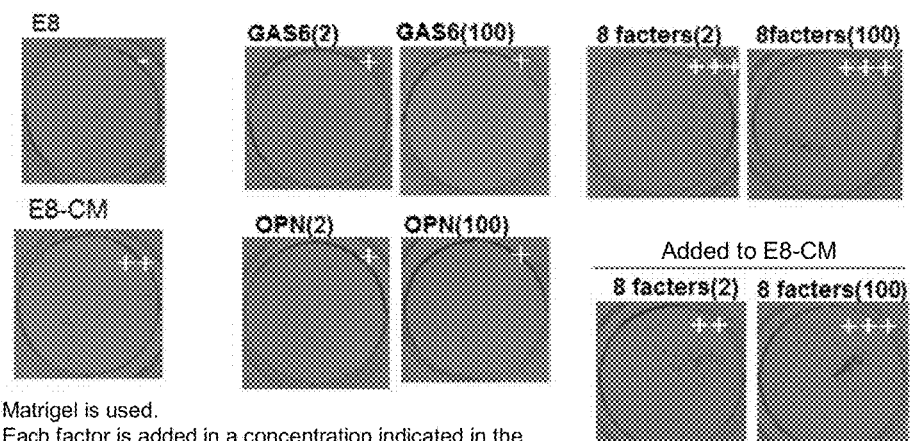
Matrigel is used.
Each factor is added in a concentration indicated in the
parentheses (unit: ng/ml) to E8 medium.
After culture for 2 days, the resultant is stained with AP.

[Figure 3]
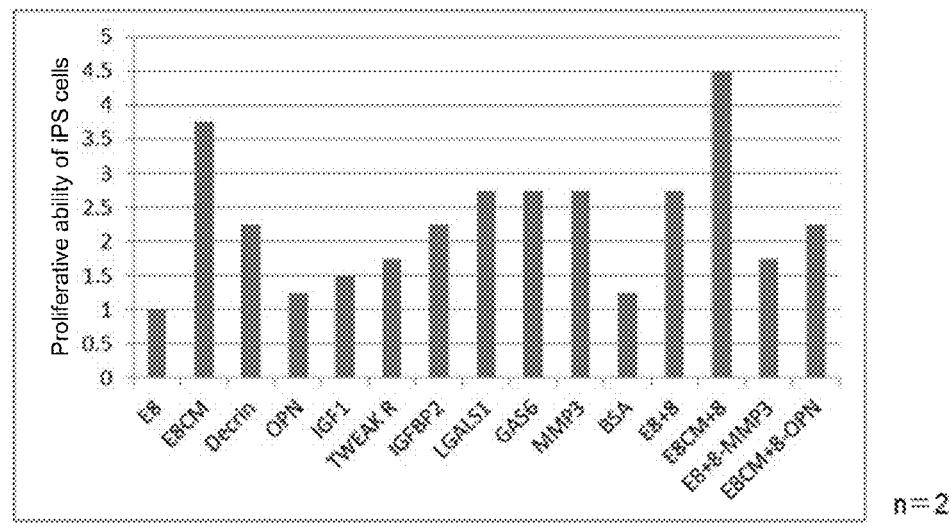
[Figure 4]
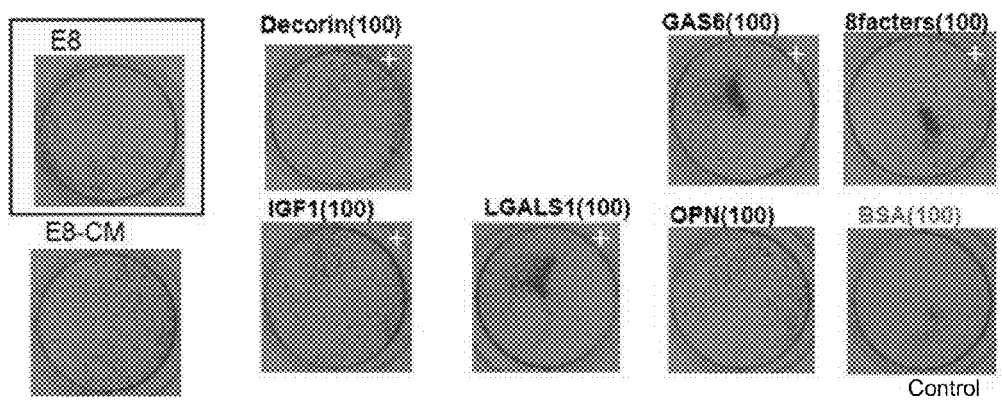
Matrigel is used.
Each factor is added in a concentration indicated in the parentheses (unit: ng/ml) to E8 medium.
After culture for 2 days, the resultant is stained with AP.

[Figure 5]
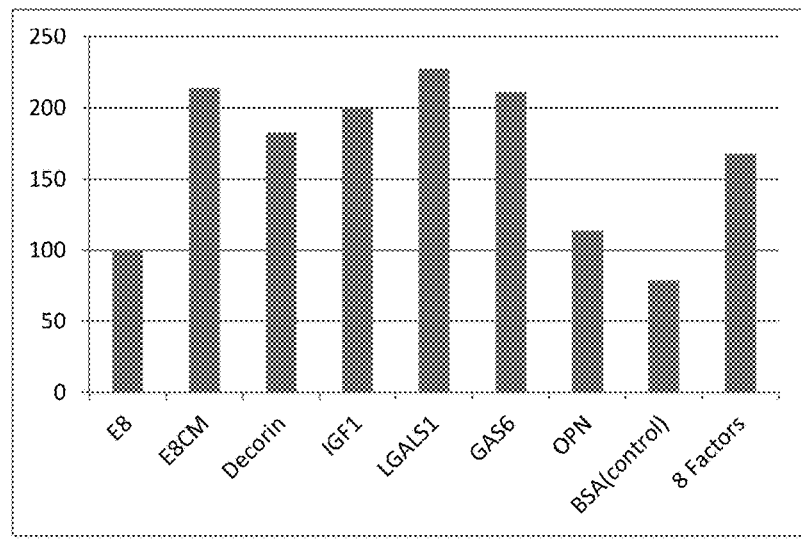
[Figure 6]
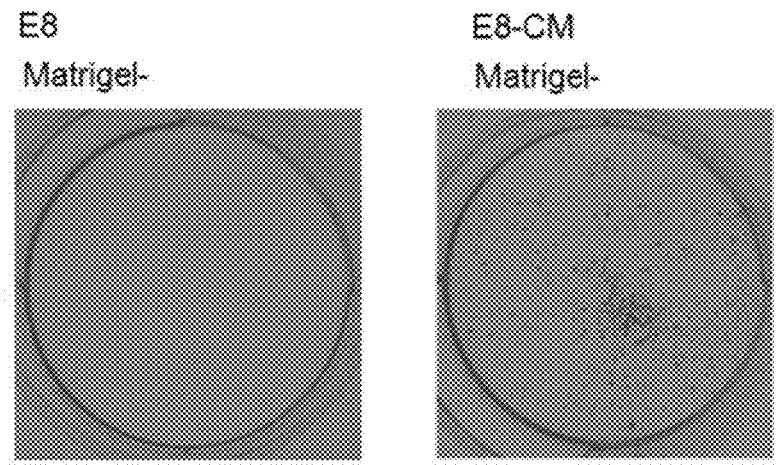
The cells adhere to E8CM without using matrices.

[Figure 7]
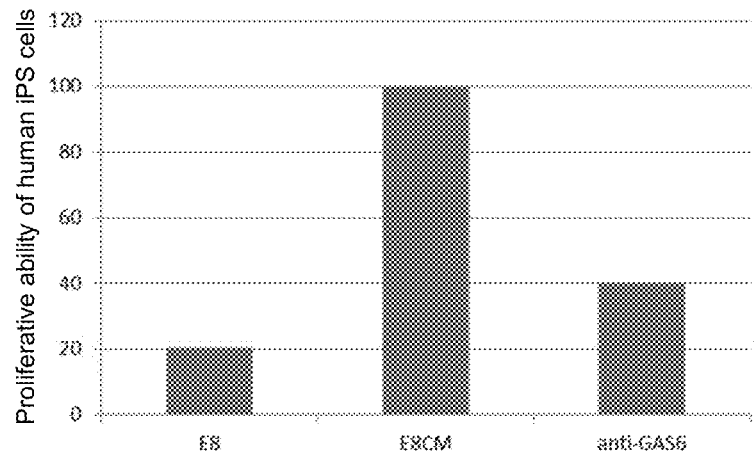
[Figure 8]
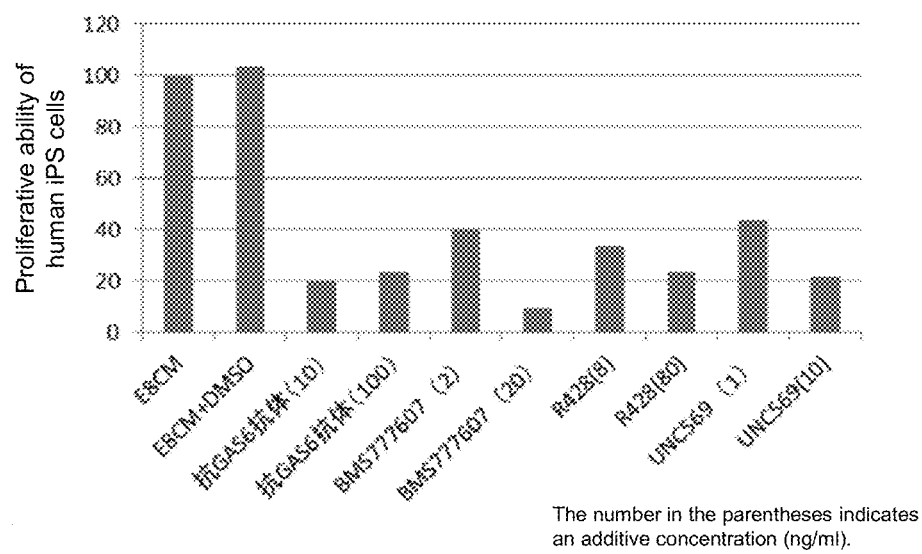
The number in the parentheses indicates an additive concentration (ng/ml).

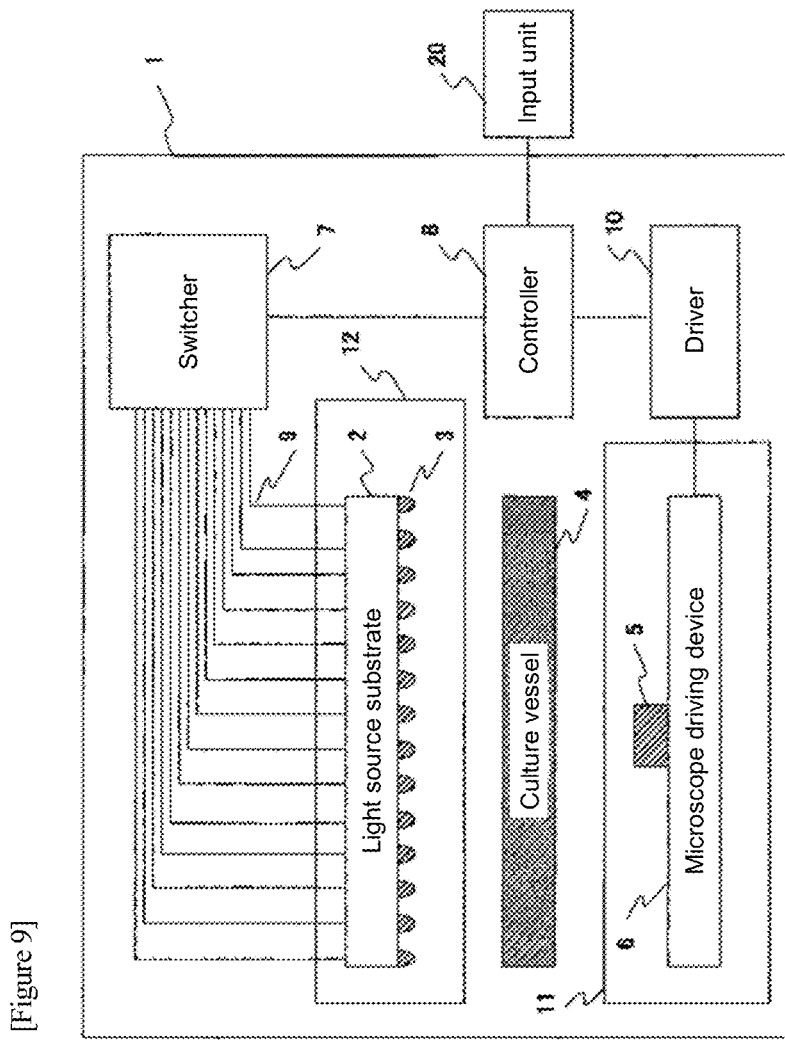
[Figure 9]

[Figure 10]
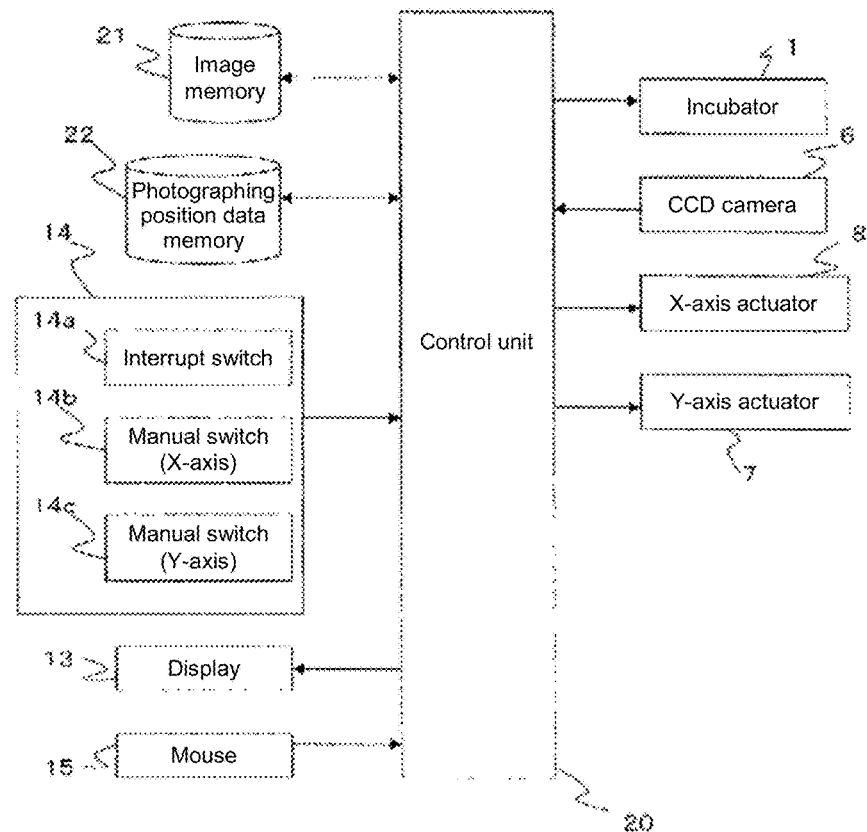
[Figure 11]
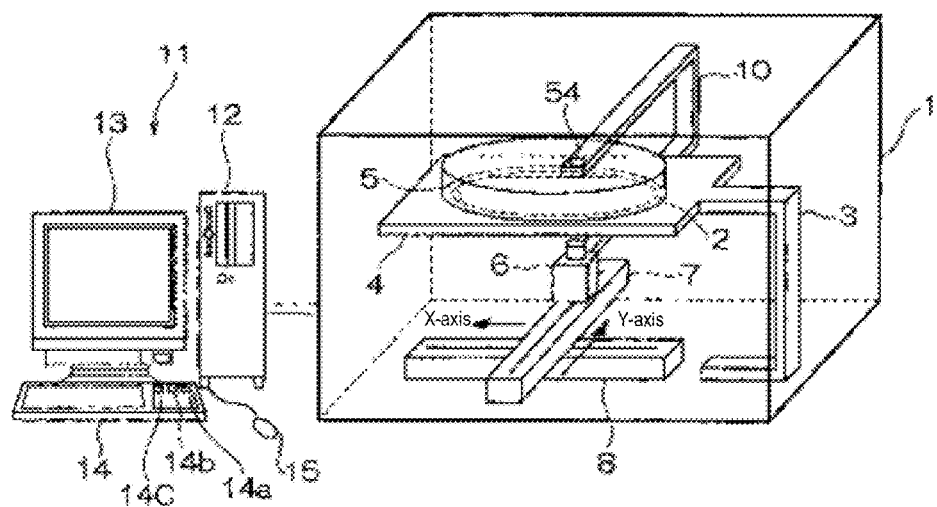

[Figure 12]
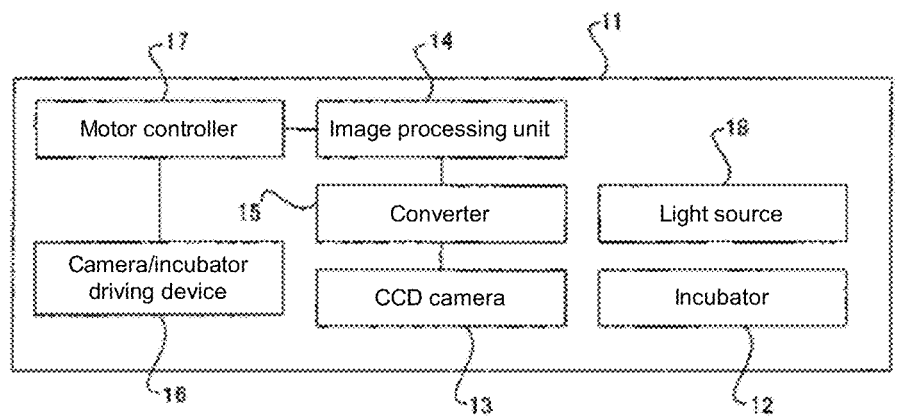
[Figure 13]
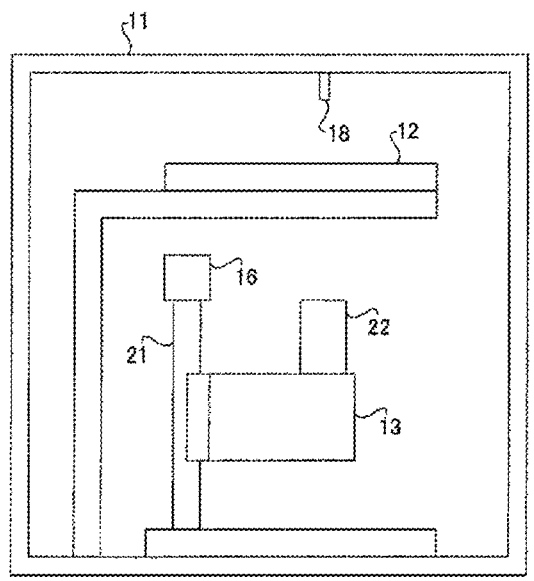

[Figure 14]
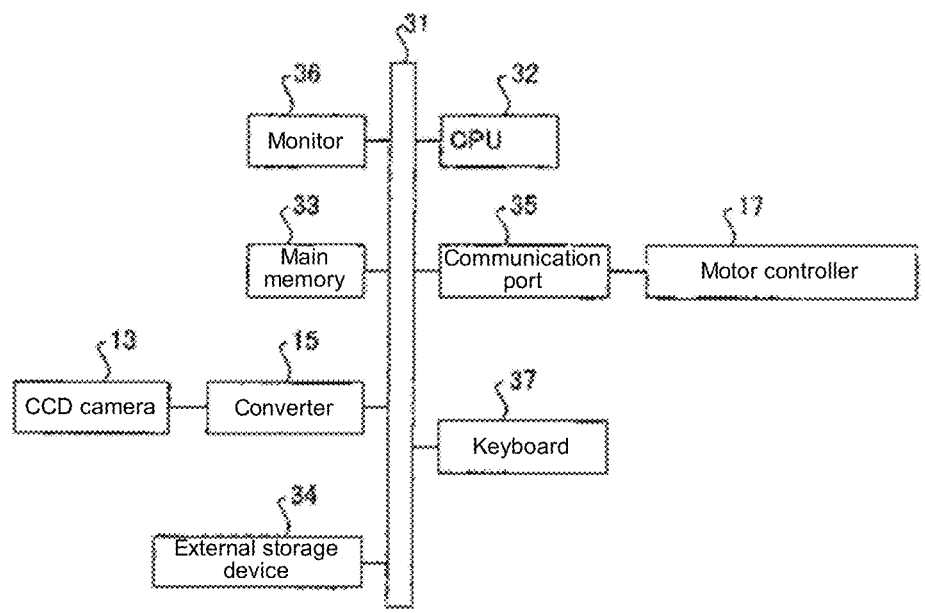

[Figure 15]
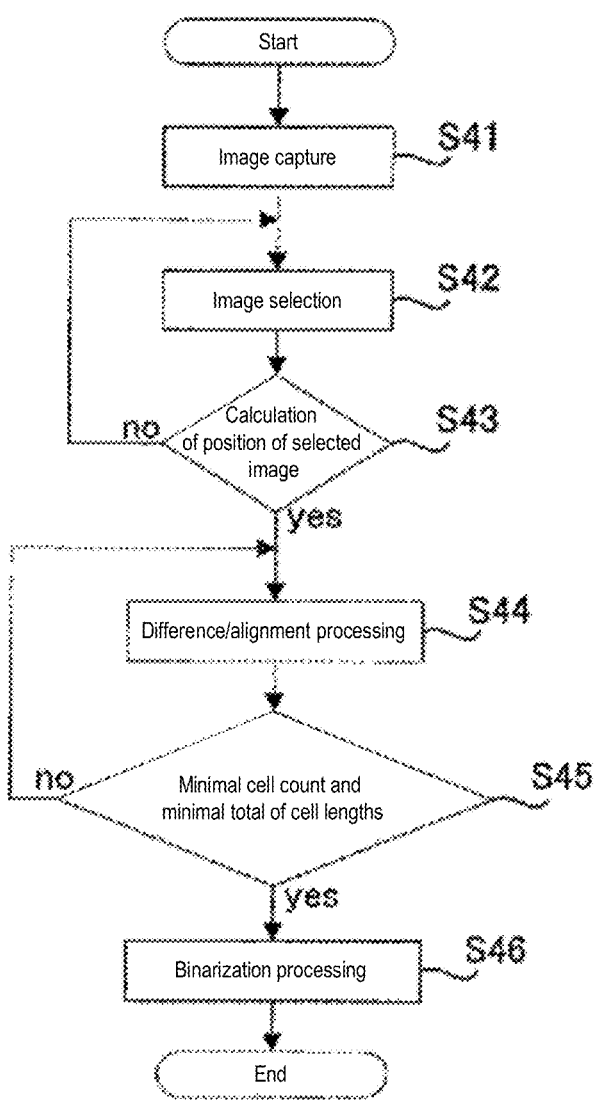

CELL CULTURE MEDIUM AND CULTURE METHOD USING THE SAME

TECHNICAL FIELD

The present invention relates to a cell culture medium and a method for culturing cells. Also, the present invention relates to feeder cells that can be used in the aforementioned culture method, and a method for evaluating a medium for culturing cells.

BACKGROUND ART

As a result of recent studies, the possibility of practical use of human pluripotent stem cells such as human ES cells (hESC) or human iPS cells (hiPSC) has been increased in the field of regenerative medicine. These human pluripotent stem cells have an infinite proliferative ability and an ability to differentiate into various cells, and thus, the cells are expected as a therapeutic means for treating intractable disease, lifestyle-related disease and the like. It has been demonstrated that human pluripotent stem cells can be induced to differentiate in vitro into a variety of cells such as nerve cells, cardiomyocytes, blood cells, or retinal cells.

Feeder cells act to supply a growth factor for the maintenance culture of human pluripotent stem cells to stein cells. Thus, human pluripotent stem cells such as hESC or hiPSC have been conventionally cultured mainly on a layer of mouse-derived feeder cells (MEF: mouse embryonic fibroblasts). Activity of performing the maintenance culture of human pluripotent stein cells has also been reported for various human cells (Non Patent Literatures 1 to 4). However, the method of using mouse-derived feeder cells has been problematic in terms of safety to living bodies because the feeder cells are mixed into human pluripotent stem cells. In addition, a culture method of using human-derived feeder cells has also been problematic in terms of time-consuming preparation of feeder cells upon culture.

As methods for culturing human pluripotent stem cells without using feeder cells such as MEF, a method of previously conditioning a medium with MEF (MEF-CM) and a method of chemically immobilizing MEF on a medium have been known (Non Patent Literature 5). Moreover, a method of using, as living feeder cells, various human-derived cells such as fibroblasts, placental cells, bone marrow cells or endometrial cells, without using heterologous cells, has also been reported (Non Patent Literature 6). Furthermore, in order to culture human pluripotent stem cells, a medium containing bovine serum, KNOCKOUT™ SR (Knockout Serum Replacement: an additive that can be used, instead of serum, to culture ES/iPS cells), and the like has been used. However, such a medium often contains a protein extracted from bovine serum, and thus, it has been concerned about infectious diseases such as bovine spongiform encephalopathy (BSE) or cell contamination caused by virus. There is a case where human-derived serum is used, but since such human-derived serum has restrictions and limitations on use, it is not suitable for practical use. Further, it has been known that human pluripotent stem cells can be cultured in the absence of feeder cells by using a medium for human pluripotent stem cells containing such serum or a serum replacement, which has been conditioned with MEF. However, it has been difficult to identify a factor useful for the growth of human pluripotent stem cells, which is secreted from MEF, in a medium containing a large amount of serum-derived protein. In order to identify such a factor, a receptor protein that changes specifically in human ES cells cultured in MEF-CM has also been analyzed (Non Patent Literature 7).

The development of a chemically defined medium for carrying out a culture without using MEF has also been promoted, and the problem regarding contamination with bovine serum-derived components has been almost avoided (Non Patent Literatures 8 and 9). Using an MEF secretion, the analysis of functional proteins has been carried out (Non Patent Literature 10). Also, it has been reported that embryonic stem cells can be cultured without using feeder cells by addition of vitronectin and IGF1 chimeric protein (Non Patent Literature 11). As commercially available IGF-containing media, mTeSR1 (registered trademark) manufactured by STEM CELL Technologies, STEMPRO (registered trademark) manufactured by Life Technologies, and the like have been known. However, these media have been problematic in that human pluripotent stem cells cannot be stably cultured therein, and in that they exhibit poor proliferative ability therein.

On the other hand, Patent Literature 1 describes a method for producing a composition comprising a Vitamin K-dependent protein of interest with a substantially lower amount of at least one protein contaminant expressed endogenous by the host cell in the absence of modification, the method comprising the steps of a) producing a host cell according to the invention; and b) growing the host cell in a growth medium and harvesting the growth medium comprising the Vitamin K-dependent protein of interest. Patent Literature 1 also describes GAS-6 as an example of the vitamin K-dependent protein (paragraphs 0008 and 0035). Patent Literature 2 describes that cells are cultured in a medium containing 10% FCS and GAS6 when a scratch assay is carried out (paragraph 0059). In addition, Patent Literature 3 describes that gas6 is added as a neuron growth enhancer to a medium (paragraph 0235). However, there have been no reports regarding addition of GAS6 to a serum-free medium.

Moreover, GAS6 has been clarified to be a ligand for receptor tyrosine kinase (Non Patent Literature 12). The receptor tyrosine kinase includes EGFR, ERBB2, ERBB3, ERBB4, INSR, IGF-1R, IRR, PDGFRα, PDGFRβ, CSF-1R, KIT/SCFR, FLK2/FLT3, VEGRF 1 to 3, FGFR1 to 4, CCK4, TRKA, TRKB, TRKC, MET, RON, EPHA 1 to 8, EPHB 1 to 6, AXL, MER, TYRO3, TIE, TEK, RYK, DDR1, DDR2, RET, ROS, LTK, ALK, ROR1, ROR2, MUSK, AATYK, AATYK2, AATYK3, RTK106, and the like. It has been reported that GAS6 functions as a ligand for receptor tyrosine kinase belonging to the TAM family (TYRO3, AXL, and MER) (Non Patent Literature 13).

PRIOR ART LITERATURES

Patent Literatures

Patent Literature 1: JP Patent Publication (Kohyo) No. 2009-501014 A
Patent Literature 2: JP Patent Publication (Kohyo) No. 2005-532805 A
Patent Literature 3: JP Patent Publication (Kokai) No. 2009-77716 A

Non Patent Literatures

Non Patent Literature 1: Hovatta O, Mikkola M, Gertow K et al., A culture system using human foreskin fibroblasts as feeder cells allows production of human embryonic stem cells. Hum Reprod 2003; 18: 1404-1409.

Non Patent Literature 2: Richards M, Fong C Y, Chan W K et al., Human feeders support prolonged undifferentiated growth of human inner cell masses and embryonic stem cells. Nat Biotechnol 2002; 20: 933-936.

Non Patent Literature 3: Cheng L, Hammond H, Ye Z et al., Human adult marrow cells support prolonged expansion of human embryonic stem cells in culture. Stem Cells 2003; 21: 131-142.

Non Patent Literature 4: Richards M, Tan S, Fong C Y et al., Comparative evaluation of various human feeders for prolonged undifferentiated growth of human embryonic stem cells. Stem Cells 2003; 21: 546-556.

Non Patent Literature 5: Yue X-S, Fujishiro M, Nishioka C, Arai T, Takahashi E, Gong J-S, Akaike T, Ito Y., Feeder cells support the culture of induced pluripotent stem cells even after chemical fixation. PLoS ONE 2012; 7: e32707.

Non Patent Literature 6: Hayato Fukusumi, Yonehiro Kanemura, Development of feeder cell-free culture technique of human ES/iPS cells, *Igaku no Ayumi* (Progress of Medicine), 2011; 239: 1338-1344.

Non Patent Literature 7: Wang L, Schulz T C, Sherrer E S, Dauphin D S, Shin S et al., Self-renewal of human embryonic stem cells requires insulin-like growth factor-1 receptor and ERBB2 receptor signaling. Blood 2007; 110: 4111-4119.

Non Patent Literature 8: Veronika A, Peter W A, Stephen B, Nissim B, Jennifer B et al., Comparison of defined culture systems for feeder cell free propagation of human embryonic stem cells. In Vitro Cell Dev Biol Anim. 2010; 46: 247-58.

Non Patent Literature 9: Chen G, Gulbranson D R, Hou Z, Bolin J M, Ruotti V, Probasco M D et al., Chemically defined conditions for human iPSC derivation and culture. Nat Methods. 2011; 8: 424-429.

Non Patent Literature 10: Chin A C, Fong W J, Goh L T, Philp R, Oh S K, Choo A B. Identification of proteins from feeder conditioned medium that support human embryonic stem cells. Journal of Biotechnology, 2007; 130: 320-8.

Non Patent Literature 11: Manton K J, Richards S, Van Lonkhuyzen D, Cormack L, Leavesley D, Upton Z, A chimeric vitronectin: IGF-I protein supports feeder-cell-free and serum-free culture of human embryonic stem cells, Stem Cells Dev. 2010, 19(9): 1297-1305

Non Patent Literature 12: Junichi Shimoda, Takayoshi Hamamoto, Gas6-deficient mice, Japanese Journal of Thrombosis and Hemostasis, 2001; 12(6): 514-521.

Non Patent Literature 13: Vyacheslav A K. Axl-dependent signaling: a clinical update. Clinical science 2012; 122: 361-368.

SUMMARY OF INVENTION

Object to be Solved by the Invention

It is an object to be solved by the present invention to provide a cell culture medium capable of enhancing cell growth efficiency without using feeder cells, in particular which contains no serum. In addition, it is another object to be solved by the present invention to provide a method for culturing cells using the aforementioned cell culture medium.

Means for Solving the Object

As a result of intensive studies directed towards achieving the aforementioned objects, the present inventor has found that the growth of human pluripotent stem cells can be promoted by adding GAS6 to a serum-free medium used for human pluripotent stem cells, without co-culturing the human pluripotent stem cells with feeder cells, thereby completing the present invention. Specifically, according to the present invention, GAS6 has been identified as a factor for promoting the growth of human pluripotent stem cells.

According to the present invention, the following inventions are provided.

(1) A cell culture medium, which comprises growth arrest-specific 6 (GAS6) and does not comprise serum.

(2) The cell culture medium according to (1) above, wherein the concentration of the growth arrest-specific 6 (GAS6) contained in the medium is 2 ng/ml or more and 100 ng/ml or less.

(3) The cell culture medium according to (1) or (2) above, which further comprises at least one selected from the group consisting of decorin, matrix metalloproteinase-3 (MMP3), osteopontin (OPN), TNF-related weak inducer of apoptosis receptor (TWEAK R), insulin-like growth factor-binding protein 2 (IGFBP2), galectin 1 (LGALS1), and insulin-like growth factor-1 (IGF-1).

(4) The cell culture medium according to any one of (1) to (3) above, which does not comprise albumin.

(5) The cell culture medium according to any one of (1) to (4) above, wherein the cells are mouse-derived cells or human-derived cells.

(6) The cell culture medium according to any one of (1) to (5) above, wherein the cells are pluripotent stem cells.

(7) The cell culture medium according to (6) above, wherein the pluripotent stem cells are iPS cells (induced pluripotent stem cells).

(8) A cell medium kit, which comprises growth arrest-specific 6 (GAS6) and a basal medium.

(9) The cell medium kit according to (8) above, wherein the basal medium is Essential 8 (registered trademark) medium.

(10) The cell medium kit according to (8) or (9) above, which further comprises at least one selected from the group consisting of decorin, matrix metalloproteinase-3 (MMP3), osteopontin (OPN), TNF-related weak inducer of apoptosis receptor (TWEAK R), insulin-like growth factor-binding protein 2 (IGFBP2), galectin 1 (LGALS1), and insulin-like growth factor-1 (IGF-1).

(11) The cell medium kit according to any one of (8) to (10) above, wherein the cells are mouse-derived cells or human-derived cells.

(12) The cell medium kit according to any one of (8) to (11) above, wherein the cells are pluripotent stem cells.

(13) The cell medium kit according to (12) above, wherein the pluripotent stem cells are iPS cells or ES cells.

(14) A cell culture system, which comprises: (a) the cell culture medium according to any one of (1) to (7) above or the cell medium kit according to any one of (8) to (13) above; and (b) a cell culture apparatus.

(15) A method for culturing cells, which comprises culturing cells, using any of the cell culture medium according to any one of (1) to (7) above, the cell medium kit according to any one of (8) to (13) above, or the cell culture system according to (14) above.

(16) The culture method according to (15) above, wherein the cells are cultured in the absence of feeder cells.

(17) The culture method according to (15) or (16) above, wherein the cells are cultured on a culture substrate having a surface that has not been coated with an extracellular matrix.

(18) The culture method according to (15) or (16) above, wherein the cells are cultured on a culture substrate coated with an extracellular matrix.

(19) The culture method according to (17) or (18) above, wherein the extracellular matrix is any one or more selected from the group consisting of gelatin, Matrigel that is an isolated basement membrane component generated from Engelbreth-Holm-Swarm (EHS) mouse sarcoma, placenta matrix, merosin, tenascin, heparin sulfate, chondroitin sulfate, dermatan sulfate, aggrecan, biglycan, thrombospondin, laminin (laminin-511, laminin-111, and laminin-332), fibronectin, vitronectin, collagen, E-cadherin, decorin, a synthetic peptide, a synthetic polymer, and an extracellular matrix derived from MEF or human serum or decidua mesenchymal cells.

(20) The culture method according to any one of (15) to (19) above, wherein the cells are mouse-derived cells or human-derived cells.

(21) The culture method according to any one of (15) to (20) above, wherein the cells are pluripotent stem cells.

(22) The culture method according to (21) above, wherein the pluripotent stem cells are iPS cells (induced pluripotent stem cells).

(23) A method for culturing cells, which comprises culturing cells in the presence of feeder cells, into which a nucleotide sequence encoding the amino acid sequence of growth arrest-specific 6 (GAS6) has been introduced.

(24) The culture method according to (23) above, wherein the feeder cells are selected from the group consisting of MEF (mouse embryonic fibroblasts), STO cell line (ATCC Accession No. CRL-1503), fibroblasts, placental cells, bone marrow cells, and endometrial cells.

(25) The culture method according to (23) or (24) above, wherein the cells are mouse-derived cells or human-derived cells.

(26) The culture method according to any one of (23) to (25) above, wherein the cells are pluripotent stem cells.

(27) The culture method according to (26) above, wherein the pluripotent stem cells are iPS cells (induced pluripotent stem cells).

(28) Feeder cells, into which a nucleotide sequence encoding the amino acid sequence of growth arrest-specific 6 (GAS6) has been introduced.

(29) The feeder cells according to (28) above, which are selected from the group consisting of MEF (mouse embryonic fibroblast), STO cell line (ATCC Accession No. CRL-1503), fibroblasts, placental cells, bone marrow cells, and endometrial cells.

(30) A method for evaluating a medium for culturing cells, which comprises detecting or quantifying growth arrest-specific 6 (GAS6) contained in the medium.

(31) A growth inhibitor for pluripotent stem cells, which comprises an anti-GAS6 antibody or a GAS6 receptor tyrosine kinase inhibitor.

(32) The growth inhibitor according to (31) above, wherein the GAS6 receptor tyrosine kinase inhibitor is one or more selected from among: BMS777607
[N-(4-((2-amino-3-chloropyridin-4-yl)oxy)-3-fluorophenyl)-4-ethoxy-1-(4-fluorophenyl)-2-oxo-1,2-dihydropyridine-3-carboxamide];
R428
[1-(6,7-dihydro-5H-benzo[2,3]cyclohepta[2,4-d]pyridazin-3-yl)-3-N-[(7S)-7-pyrrolidin-1-yl-6,7,8,9-tetrahydro-5H-benzo[7]annulen-3-yl]-1,2,4-triazole-3,5-diamine]; and
UNC569
[1-((trans-4-aminocyclohexyl)methyl)-N-butyl-3-(4-fluorophenyl)-1H-pyrazolo[3,4-d]pyrimidin-6-amine].

(33) The growth inhibitor according to (31) or (32) above, wherein the pluripotent stem cells are iPS cells (induced pluripotent stem cells).

(34) A cell culture medium, which comprises the growth inhibitor according to any one of (31) to (33) above.

(35) A cell medium kit, which comprises the growth inhibitor according to any one of (31) to (33) above and a basal medium.

(36) A cell culture system, which comprises: (a) the cell culture medium according to (34) above or the cell medium kit according to (35) above; and (b) a cell culture apparatus.

(37) A method for culturing cells, which comprises culturing cells, using any of the cell culture medium according to (34) above, the cell medium kit according to (35) above, and the cell culture system according to (36) above.

(38) A method for culturing pluripotent stem cells, which comprises culturing pluripotent stem cells under conditions in which the action of GAS6 is inhibited.

(39) The culture method according to (38) above, wherein the culturing of pluripotent stem cells under conditions in which the action of GAS6 is inhibited is a culturing of pluripotent stem cells in the presence of an anti-GAS6 antibody and/or a GAS6 receptor tyrosine kinase inhibitor.

(40) The culture method according to (39) above, wherein the GAS6 receptor tyrosine kinase inhibitor is one or more selected from among:
BMS777607
[N-(4-((2-amino-3-chloropyridin-4-yl)oxy)-3-fluorophenyl)-4-ethoxy-1-(4-fluorophenyl)-2-oxo-1,2-dihydropyridine-3-carboxamide];
R428
[1-(6,7-dihydro-5H-benzo[2,3]cyclohepta[2,4-d]pyridazin-3-yl)-3-N-[(7S)-7-pyrrolidin-1-yl-6,7,8,9-tetrahydro-5H-benzo[7]annulen-3-yl]-1,2,4-triazole-3,5-diamine]; and
UNC569
[1-((trans-4-aminocyclohexyl)methyl)-N-butyl-3-(4-fluorophenyl)-1H-pyrazolo[3,4-d]pyrimidin-6-amine].

(41) The culture method according to (39) above, wherein the concentration of the anti-GAS6 antibody contained in a medium for culturing pluripotent stem cells is 10 ng/ml or more and 100 ng/ml or less.

(42) The culture method according to (40) above, wherein when a medium for culturing pluripotent stem cells comprises BMS777607, the concentration of the BMS777607 contained in the medium is 2 ng/ml or more and 20 ng/ml or less, when a medium for culturing pluripotent stem cells comprises R428, the concentration of the R428 contained in the medium is 8 ng/ml or more and 80 ng/ml or less, and when a medium for culturing pluripotent stem cells comprises UNC569, the concentration of the UNC569 contained in the medium is 1 ng/ml or more and 10 ng/ml or less.

(43) The culture method according to any one of (38) to (42) above, wherein the pluripotent stem cells are iPS cells (induced pluripotent stem cells).

(44) The culture method according to any one of (38) to (43) above, wherein the pluripotent stem cells are cultured in a medium, which does not comprise albumin.

(45) The culture method according to any one of (38) to (44) above, wherein the pluripotent stem cells are cultured in a medium, which does not comprise serum.

(46) The culture method according to any one of (38) to (45) above, wherein the pluripotent stem cells are cultured in a medium comprising GAS6.

(47) The culture method according to any one of (38) to (46) above, wherein the pluripotent stem cells are cultured in a medium conditioned with MEF.

Advantageous Effects of Invention

By culturing cells using the cell culture medium of the present invention, it becomes possible to allow cells such as pluripotent stem cells to efficiently grow. According to the cell culture medium of the present invention, cells can be cultured without using feeder cells, and thus, the cells can be safely cultured.

BRIEF DESCRIPTION OF DRAWINGS

FIG. 1 shows comparative results regarding the growth efficiencies of human iPS cells in a serum-free medium, in a serum-free medium conditioned with MEF, or in serum-free media to which various types of protein factors have been added, which are compared by staining with alkaline phosphatase.

FIG. 2 shows comparative results regarding the growth efficiencies of human iPS cells in a serum-free medium, in a serum-free medium conditioned with MEF, or in serum-free media to which various types of protein factors have been added, which are compared by staining with alkaline phosphatase.

FIG. 3 shows the results obtained by counting the number of human iPS cells in a serum-free medium, in a serum-free medium conditioned with MEF, or in serum-free media to which various types of protein factors have been added, and then comparing the obtained numbers.

FIG. 4 shows comparative results regarding the growth efficiencies of human iPS cells in a serum-free medium, in a serum-free medium conditioned with MEF, or in serum-free media to which various types of protein factors have been added, which are compared by staining with alkaline phosphatase.

FIG. 5 shows the results obtained by counting the number of human iPS cells in a serum-free medium, in a serum-free medium conditioned with MEF, or in serum-free media to which various types of protein factors have been added, and then comparing the obtained numbers.

FIG. 6 shows comparative results regarding the growth efficiencies of human iPS cells, which have been cultured in a serum-free medium or in a serum-free medium conditioned with MEF, without using Matrigel, and which have been then compared by staining with alkaline phosphatase.

FIG. 7 shows the results obtained by counting the number of human iPS cells in a serum-free medium, in a serum-free medium conditioned with MEF, or in a medium conditioned with MEF, to which an anti-GAS antibody has been added, and then comparing the obtained numbers.

FIG. 8 shows the results obtained by counting the number of human iPS cells in a serum-free medium, in a serum-free medium conditioned with MEF, or in media conditioned with MEF, to which various types of GAS6 receptor tyrosine kinase inhibitors have been added, and then comparing the obtained numbers.

FIG. 9 shows an outline configuration of individual constitutional elements of a culture apparatus.

FIG. 10 shows a block diagram of an observation device for an automatic culture apparatus.

FIG. 11 shows a configuration of hardware forming a main part of an automatic culture apparatus.

FIG. 12 shows a configuration of a cell detection system of a cell culture apparatus.

FIG. 13 shows an outline configuration of individual constitutional elements of a culture apparatus.

FIG. 14 shows details of an image processing unit.

FIG. 15 shows an example of a cell extraction treatment conducted by an image processing unit.

EMBODIMENTS FOR CARRYING OUT THE INVENTION

Hereinafter, the embodiments of the present invention will be described.

The cell culture medium of the present invention is characterized in that it contains growth arrest-specific 6 (GAS6) and does not contain serum. By adding growth arrest-specific 6 (GAS6) to a medium, the growth of human pluripotent stem cells can be promoted without using serum and feeder cells. Thereby, human pluripotent stem cells, which are not exposed to either animal cells or a culture solution conditioned with such animal cells, can be easily cultured.

The concentration of growth arrest-specific 6 (GAS6) contained in the medium is not particularly limited, as long as cells are able to grow in the presence of GAS6. Taking into consideration addition effect, in general, the lower limit of the concentration is 0.0001 ng/ml, preferably 0.001 ng/ml, more preferably 0.01 ng/ml, even more preferably 0.1 ng ml, particularly preferably 1 ng/ml, and most preferably 2 ng/ml. Taking into consideration costs, the upper limit of the concentration is 10000 ng/ml, preferably 1000 ng/ml, more preferably 500 ng/ml, even more preferably 400 ng/ml, particularly preferably 300 ng/ml, more particularly preferably 200 ng/ml or less, and even more particularly preferably 100 ng/ml or less. The concentration of GAS6 is generally 1 ng/ml or more and 200 ng/ml or less, and particularly preferably 2 ng/ml or more and 100 ng/ml or less.

The cell culture medium of the present invention is characterized in that cell growth can be promoted and cells can be stably cultured in a medium, which does not comprise serum (namely, a serum-derived component). The medium that can be used in the present invention can be prepared using a medium used for animal cells as a basal medium. The basal medium is not particularly limited, as long as it can be used for the culture of animal cells. Examples of the basal medium include, but are not particularly limited to, BME medium, BGJb medium, CMRL1066 medium, Glasgow MEM medium, Improved MEM Zinc Option medium, DMEM medium, Medium 199 medium, Eagle MEM medium, αMEM medium, DMEM medium, Ham medium, RPMI 1640 medium, Fischer's medium, and a mixed medium thereof. Specific examples include media containing no serum-derived components, to which insulin and transferrin are added, such as CHO-S-SFM II (manufactured by GIBCO BRL), Hybridoma-SFM (manufactured by GIBCO BRL), eRDF Dry Powdered Media (manufactured by GIBCO BRL), UltraCULTURE™ (manufactured by BioWhittaker), UltraDOMA™ (manufactured by BioWhittaker), UltraCHO™ (manufactured by BioWhittaker), and UltraMDCK™ (manufactured by BioWhittaker). Essential 8 (manufactured by Life Technologies), STEMPRO hESC SFM (manufactured by Life Technologies), mTeSR1 (manufactured by Veritas), TeSR2 (manufactured by Veritas), and ReproXF (manufactured by ReproCELL), all of which have been developed for use in the culture of human pluripotent stem cells, are optimal media. Particularly preferably, DMEM/F12 (1:1) medium or Essential 8 (manufactured by Life Technologies), to which ITS (insulin, transferrin, and selenium), human FGF2, TGF-β1, ascorbyl-2-phosphate magnesium, and sodium hydrogen carbonate are added, can be used.

To the cell culture medium of the present invention, an MEF secretion component may be further added. Specifically, at least one selected from the group consisting of decorin, matrix metalloproteinase-3 (MMP3), osteopontin (OPN), TNF-related weak inducer of apoptosis receptor (TWEAK R), insulin-like growth factor-binding protein 2 (IGFBP2), galectin 1 (LGALS1), and insulin-like growth factor-1 (IGF-1) may be added as an MEF secretion component.

Among such MEF secretion components, which can be added to the present culture medium in addition to growth arrest-specific 6 (GAS6), at least one selected from the group consisting of decorin, galectin 1 (LGALS1), and insulin-like growth factor-1 (IGF-1) can be preferably added. For example, such MEF secretion components and GAS6 can be added in combination of "GAS6 and decorin," "GAS6 and LGALS1," "GAS6 and IGF-1," "GAS6, decorin and LGALS1," "GAS6, decorin and IGF-1," "GAS6, LGALS1 and IGF-1," or "GAS6, decorin, LGALS1 and IGF-1," etc.

It is to be noted that since decorin, galectin 1 (LGALS1), and insulin-like growth factor-1 (IGF-1) exhibit the effect of promoting cell growth, even in a case where they are added alone, it is also possible to add merely one or more factors selected from the group consisting of decorin, galectin 1 (LGALS1) and insulin-like growth factor-1 (IGF-1) to the cell culture medium.

When the above-described MEF secretion component is added to the cell culture medium, the concentration of each component contained in the medium is not particularly limited, as long as cells can proliferate therein. Taking into consideration addition effect, in general, the lower limit of the concentration is 0.0001 ng/ml, preferably 0.001 ng/ml, more preferably 0.01 ng/ml, even more preferably 0.1 ng/ml, particularly preferably 1 ng/ml, and most preferably 2 ng/ml. Taking into consideration costs, the upper limit of the concentration is 10000 ng/ml, preferably 1000 ng/ml, more preferably 500 ng/ml, even more preferably 400 ng/ml, particularly preferably 300 ng/ml, more particularly preferably 200 ng/ml or less, and even more particularly preferably 100 ng/ml or less. The concentration of the component is generally 1 ng/ml or more and 200 ng/ml or less, and particularly preferably 2 ng/ml or more and 100 ng/ml or less.

The cell culture medium of the present invention preferably does not comprise albumin.

The cell culture medium of the present invention may comprise, as appropriate, transferrin, fatty acid, insulin, a collagen precursor, a trace element, 2-mercaptoethanol, 3-thiolglycerol, or an equivalent thereof.

The medium of the present invention may also comprise fatty acid or lipid, amino acid (e.g., non-essential amino acid), vitamin, a growth factor, cytokine, an antioxidant, 2-mercaptoethanol, pyruvic acid, a buffer agent, inorganic salts, etc. For example, the concentration of 2-mercaptoethanol is not limited, as long as it is used in a concentration suitable for the culture of stem cells. It can be used in a concentration of, for example, approximately 0.05 to 1.0 mM, and preferably approximately 0.1 to 0.5 mM.

As described above, the cell culture medium of the present invention can be produced by adding GAS6 to a basal medium. The present cell culture medium can also be used in the form of a cell medium kit, which comprises GAS6 and a basal medium. Specifically, a kit comprising GAS6 and a basal medium, wherein the GAS6 and the basal medium are placed separately, is provided, and when the kit is used, a user adds the GAS6 to the basal medium to prepare the cell culture medium of the present invention, so that the prepared cell culture medium can be used.

Moreover, according to the present invention, a cell culture system comprising (a) the above-described cell culture medium or cell medium kit and (b) a cell culture apparatus is provided.

The cell culture apparatus is not limited, as long as it is an apparatus capable of culturing cells using the above-described cell culture medium or cell medium kit. For instance, the cell culture apparatuses described in JP Patent Publication (Kokai) No. 2008-92811 A, JP Patent Publication (Kokai) No. 2008-92882 A, and JP Patent Publication (Kokai) No. 2010-148391 A (the content described in the aforementioned publications is incorporated herein as a part of the disclosure of the present description) can be used.

As an example of the present invention, there can be used a cell culture apparatus comprising a culture vessel for culturing cells, an imaging device for taking an image of the cells in the culture vessel, a light source means for applying light to the cells when an image of the cells is taken, and a moving means for moving the microscope, as described in JP Patent Publication (Kokai) No. 2008-92811 A, wherein the cell culture apparatus is characterized in that the light source means has a plurality of light sources, and in that the light source corresponding to the position of the microscope is turned on. An example of the configuration of the cell culture apparatus is shown in FIG. 9.

A cell culture apparatus 1 is composed of a culture vessel 4 for culturing cells, a microscope 5 for taking an image of the cells, a microscope driving device 6 for moving the microscope 5, a driver 10 for controlling the microscope driving device 6, a switcher 7 for turning on the power to a specific light source of a plurality of light sources 3 established on a light source substrate, based on the position information of the microscope 5, a light source wiring 9 for connecting the switcher 7 with the light sources 3, a light source substrate 2 on which the light sources 3 are aligned, and a controller 8 for controlling these components. Moreover, the culture apparatus is connected with the controller 8, and comprises an input part 20 consisting of a trackball or a keyboard. The microscope driving device 6 comprises a driving mechanism having a motor and a ball screw mechanism, and is capable of two-dimensionally moving the microscope 5 via the ball screw mechanism. Furthermore, the ball screw mechanism has a position sensor which comprises a rotary encoder or the like that detects the rotation amount of the ball screw, converts it to the position information of the microscope 5 and detects it. The position sensor detects the rotation amount of the ball screw, so that it can two-dimensionally specify the position of the microscope 5. This position information of the microscope 5 is transmitted to the controller 8 via the driver 10. The ball screw mechanism comprises a ball screw having a spiral groove and a sleeve that moves along the groove. The microscope 5 is established on the sleeve. By rotating the ball screw, the sleeve and the microscope 5 can be linearly moved. The cell culture apparatus comprises two ball screw mechanisms such that they each make a right angle, and as a result, the sleeve and the microscope 5 can be two-dimensionally moved.

As another example of the present invention, there can be used an automatic culture apparatus comprising a cell incubator, a camera for photographing cells in the incubator, a moving means for relatively moving the position of the camera with respect to the incubator along the photographed surface of the incubator, a memory for storing the image photographed by the camera, a display for displaying the image stored in the memory, and a control means that is formed to be switchable between an automatic photographing mode and a manual photographing mode, as described in JP Patent Publication (Kokai) No. 2008-92882 A, wherein the automatic culture apparatus is characterized in that the automatic photographing mode has the function of controlling the moving means and allowing the camera to scan with respect to a plurality of small sections that have been obtained by dividing the photographed surface by adjusting it to the previously determined visual field of the camera, then controlling the camera and photographing the surface to be photographed at a small section unit, then storing the photographed image in the memory, then reading out the image stored in the memory, and then allowing the display to display the entire image of the photographed surface, and (a) the manual photographing mode has the function of controlling the moving means based on the operation command input by the input means and photographing the local image of the photographed surface at any given position by the camera, and at the same time, allowing the display to display the thus photographed local image, or (b) the manual photographing mode has the function of controlling the moving means and moving the position of the camera based on the position on the display designated by the input means, photographing the local image at the designated position, and allowing the display to display the photographed local image. An example of the configuration of the automatic culture apparatus is shown in each of FIG. 10 and FIG. 11.

As shown in the perspective view of FIG. 11, the present automatic culture apparatus is configured to establish a circular petri dish 2 serving as a cell incubator in an incubator 1, and in the incubator 1, a temperature and a gas concentration such as $CO_2$ are adjusted, as is publicly known. The petri dish 2 is established on a bedplate 4 supported by a stand 3, and an aperture 5, which does not hinder observation of the bottom surface of the petri dish 2 from below, is established on the bedplate 4. A CCD camera 6 for photographing cells in the petri dish 2 is established below the aperture 5 on the bedplate 4. The CCD camera 6 comprises an objective lens with a high magnification capable of observing cells. It is to be noted that a CMOS camera can be used instead of the CCD camera 6. The CCD camera 6 is mounted on a Y-axis actuator 7 for moving the camera in the Y direction indicated with the illustrated arrow. The Y-axis actuator 7 is mounted on an X-axis actuator 8 for moving the camera in the X direction with the illustrated arrow. In addition, a light source 54 is disposed at a position opposing the CCD camera 6 across the petri dish 2, and the light source 54 is fixed on the CCD camera 6, and it is equipped at the tip of a supporting arm 10. A moving means is configured to relatively move the positions of the CCD camera 6 and the light source 54 to any given positions along the bottom surface of the petri dish 2 by the Y-axis actuator 7 and the X-axis actuator 8. The CCD camera 6, the Y-axis actuator 7, the X-axis actuator 8 and the light source 54 are controlled by a computer 11 such as a personal computer (PC), and an observation device that is a feature of the present invention is composed of these components.

The computer 11 is configured by connecting a computer body 12, a display 13, a keyboard 14 and a mouse 15 serving as input means, and the like. The computer body 12 comprises CPU, memory, I/O, etc., and thus, it is comprises I/O necessary for a general purpose computer.

As shown in FIG. 10, the present apparatus comprises a control unit 20 composed of the computer body 12, and the control unit 20 is connected with the incubator 1, the CCD camera 6, the Y-axis actuator 7, the X-axis actuator 8, the display 13, the keyboard 14, and the mouse 15. An interrupt switch 14a, a manual switch (X-axis) 14b, and a manual switch (Y-axis) 14c are established on the keyboard 14. Moreover, an image memory 21 for storing the image photographed by the CCD camera 6 and a photographing position data memory 22 are connected with the control unit 20. Furthermore, the control unit 20 comprises a non-illustrative reading-out means for reading out the image stored in the image memory 21 and allowing the display 13 to display it, and a control means for controlling the photographing by the CCD camera 6 by switching it between an automatic photographing mode and a manual photographing mode.

Details for the operations performed using the present apparatus are as described in paragraphs 0029 to 0053 of JP Patent Publication (Kokai) No. 2008-92882 A.

As a further example of the present invention, as described in JP Patent Publication (Kokai) No. 2010-148391 A, there can be used a cell detection system of a cell culture apparatus comprising an incubator means for culturing cells, an image-obtaining means for obtaining the image of the cells from the incubator means, a focus position adjusting means for moving either one of the image-obtaining means and the incubator means and adjusting the focus of the image-obtaining means, and a control means for controlling the image-obtaining means such that images can be obtained at a plurality of focus positions of the image-obtaining means, wherein the cell detection system is characterized in that it comprises an image selection means for selecting an image in which the margin of a cell is seen clearly from the plurality of images obtained at the plurality of focus positions, and an extraction means for performing a subtraction treatment on a first image selected by the image selection means, in which the margin of a cell is seen clearly, and a second image obtained at a position deviated from the focus position of the first image. An example of the configuration of the cell detection system is shown in each of FIG. 12 to FIG. 15.

As shown in FIG. 12, a cell culture apparatus 11 has a box structure in which the internal portion thereof is interrupted from the external space, and in the box structure, the cell culture apparatus comprises an incubator 12 for culturing cells, a CCD camera 13 for photographing the cells in the incubator 12, an image processing unit 14 for processing the image data obtained by the CCD camera 13, a converter 15 for transferring the image data to the image processing unit 14, a camera/incubator driving device 16 for moving the CCD camera 13 or the incubator 12, a motor controller 17 for moving the camera/incubator driving device 16 to any given position, and a light source 18 established above the CCD camera 13. The incubator 12 is molded with a transparent material, and the CCD camera 13, is configured to take a photograph of a transmitted light that has been irradiated from the light source 18 and has then passed through the incubator 12. In the above-described configuration, the CCD camera 13 desirably comprises a CCD device with a resolution of approximately 40,000 pixels, and the light source 18 is not particularly limited, but it is desirably LED in the present Examples.

FIG. 13 is a view showing an outline of the arrangement of individual constitutional elements in the culture apparatus 11, and in the illustrative example, an arrangement in a case where the incubator 12 is fixed in the culture apparatus 11 and the CCD camera 13 is moved is shown. As shown in FIG. 13, the light source 18 is equipped in the upper portion of the culture apparatus 11. The incubator 12 is disposed on the lower side of this light source 18. The CCD camera 13 comprising an objective lens 22 is disposed on the lower side around the center of the incubator 12. The CCD camera 13 is vertically movably equipped in a moving guide 21, and it moves up and down along the moving guide 21 according to the drive control by the camera/incubator driving device 16 that is allowed to move by the command outputted from a CPU 32, so that it changes the focus position in the vertical direction and then takes a photograph of an image of the cells in the incubator 12. An imaging device in which the CCD camera 13 is combined with the objective lens 22 is desirably configured to be able to take a photograph of a micro area located around the bottom surface around the center of the incubator 12, for example, a micro region with a size of about 1.5 mm (depth)×2.0 mm (wide).

FIG. 14 is a view showing details of the image processing unit 14 shown in FIG. 12. The image processing unit 14 is composed of a CPU 32 for performing arithmetic processing via a data bus 31, a main memory 33 temporarily used as a storage area by the CPU 32, an external storage device 34 for storing image data or position information, a communication port 35 for communicating with a motor controller 17, a monitor 36 for displaying the image after cell extraction, and a keyboard 37 for receiving the input of the user. In this image processing unit 14, the image from the CCD camera 13 is incorporated into the unit via a converter 15, and various image processing are then carried out.

FIG. 15 is a flow chart showing an example of a cell extraction processing carried out by the image processing unit. A series of steps shown in FIG. 15 are carried out by previously installed software. That is, the steps are carried out by successively drive-controlling the units shown in FIG. 12 to FIG. 14 by the command outputted from the CPU 32, at predetermined time intervals in the cell culture process, for example, repeatedly at a frequency of once/day. As a timer for repeatedly carrying out the series of steps shown in FIG. 15 at predetermined time intervals, an output from a clock generator comprised in the CPU 32 can be used. Details for the cell extraction treatment shown in FIG. 15 are as described in paragraphs 0016 to 0028 of JP Patent Publication (Kokai) No. 2010-148391 A.

According to the present invention, a method for culturing cells, which comprises culturing cells using any of the above-described cell culture medium, cell medium kit, or cell culture system of the present invention, is provided. Moreover, safe pluripotent stem cells are provided by culturing cells using any of the cell culture medium, cell medium kit, and cell culture system of the present invention.

According to the present invention, a method for culturing cells, which comprises culturing cells using the above-described cell culture medium of the present invention, is provided.

The type of cells cultured in the present invention is not particularly limited, and the cells cultured in the present invention may be either stem cells having both pluripotency and self-proliferative ability, or differentiated cells. The cells are preferably stem cells, and more preferably pluripotent stem cells. In the present invention, the "pluripotent stem cells" mean cells that can be cultured in vitro and have pluripotency by which the cells can differentiate into all cells constituting a living body. Specific examples of the pluripotent stem cells include embryonic stem cells (ES cells), fetal gonocyte-derived pluripotent stem cells (EG cells: Proc Natl Acad Sci USA. 1998, 95: 13726-13731), testis-derived pluripotent stem cells (GS cells: Nature. 2008, 456: 344-349), and somatic cell-derived induced pluripotent stem cells (induced pluripotent stem cells; iPS cells). Furthermore, animal species, from which cells to be cultured are derived, are not particularly limited, and cells derived from any given mammals and the like can be used. For example, mouse-derived cells, human-derived cells, or the like can be used. It is to be noted that cells can be cultured under ordinary cell culture conditions.

In a preferred aspect of the present invention, cells can be cultured in the absence of feeder cells.

When pluripotent stem cells and the like are cultured without using feeder cells, the culture can be carried out using a culture vessel that has been coated with a culture substrate serving as a scaffold for cells. The culture substrate serving as a scaffold for cells is not particularly limited, as long as it is used for cell culture. Examples of the culture substrate include gelatin, Matrigel that is an isolated basement membrane component generated from Engelbreth-Holm-Swarm (EHS) mouse sarcoma, placenta matrix, merosin, tenascin, heparin sulfate, chondroitin sulfate, dermatan sulfate, aggrecan, biglycan, thrombospondin, laminin (laminin-511, laminin-ill, and laminin-332), fibronectin, vitronectin, collagen, E-cadherin, decorin, a synthetic peptide, a synthetic polymer, and an extracellular matrix derived from MEF or human serum or decidua mesenchymal cells.

Moreover, according to another aspect, cells can also be cultured using the cell culture medium of the present invention, on a culture substrate having a surface that has not been coated with the above-described extracellular matrix.

According to another aspect of the present invention, a method for culturing cells, which comprises culturing cells in the presence of feeder cells, into which a nucleotide sequence encoding the amino acid sequence of growth arrest-specific 6 (GAS6) has been introduced, is provided. Moreover, according to the present invention, feeder cells, into which a nucleotide sequence encoding the amino acid sequence of growth arrest-specific 6 (GAS6) has been introduced, are provided. That is to say, feeder cells, into which a GAS6 gene expression vector has been introduced, can be used in the on-feeder culture of human pluripotent stem cells, or can also be used in the conditioning of a medium. The type of feeder dells is not limited. Examples of the feeder cells include MEF (mouse embryonic fibroblast), the established STO cell line (ATCC Accession No. CRL-1503), mouse-derived cells, such as SNL cells, which are prepared by stably incorporating a neomycin-resistant gene expression vector and an LIF expression vector into STO cells, and human-derived cells such as fibroblasts, placental cells, bone marrow cells and endometrial cells.

Moreover, according to the present invention, a method for evaluating a medium for culturing cells, which comprises detecting or quantifying growth arrest-specific 6 (GAS6) contained in the medium, is provided. With regard to the method of detecting and quantifying the GAS6 protein, after the protein has been separated by SDS-PAGE or two-dimensional electrophoresis, it can be detected by MS analysis or a Western blot method using an anti-GAS6 antibody. Alternatively, it is also possible to quantifying the protein by an enzyme-linked immunosorbent assay (ELISA).

As described in Examples later, it has been revealed that the growth of iPS cells can be inhibited by culturing the iPS cells in the presence of an anti-GAS6 antibody or a GAS6 receptor tyrosine kinase inhibitor. Therefore, according to the present invention, a growth inhibitor for pluripotent stem cells, which comprises an anti-GAS6 antibody or a GAS6 receptor tyrosine kinase inhibitor, is provided.

Furthermore, according to the present invention, an anti-GAS6 antibody for use to inhibit the growth of pluripotent stem cells and a GAS6 receptor tyrosine kinase inhibitor for use to inhibit the growth of pluripotent stem cells are provided.

Further, according to the present invention, use of the anti-GAS6 antibody for the production of a growth inhibitor for pluripotent stem cells and use of the GAS6 receptor tyrosine kinase inhibitor for the production of a growth inhibitor for pluripotent stem cells are provided.

A cell culture medium comprising the growth inhibitor of the present invention, a cell medium kit comprising the growth inhibitor of the present invention and a basal medium, and a cell culture system comprising the cell culture medium or cell medium kit of the present invention and a cell culture apparatus are also included in the scope of the present invention. Moreover, a method for culturing cells, which comprises culturing cells using any of the cell culture medium, cell medium kit, and cell culture system of the present invention, is also included in the scope of the present invention. Constitutional elements other than the growth inhibitor and preferred ranges are as described above in the present description.

Furthermore, according to the present invention, a method for culturing pluripotent stem cells, which comprises culturing pluripotent stem cells under conditions in which the action of GAS6 is inhibited, is provided. The method for culturing pluripotent stem cells of the present invention can be carried out in vitro. By culturing pluripotent stem cells under conditions in which the action of GAS6 is inhibited, the pluripotent stem cells can be cultured in a state in which the growth thereof is inhibited. That is to say, the above-described method for culturing pluripotent stem cells according to the present invention is a method for culturing pluripotent stem cells in a state in which the growth of the pluripotent stem cells is inhibited, which comprises culturing the pluripotent stem cells under conditions in which the action of GAS6 is inhibited. Specific examples of the pluripotent stem cells are as described above in the present description, and the pluripotent stem cells are preferably iPS cells.

The type of the anti-GAS6 antibody used in the present invention is not particularly limited, and it may be either a monoclonal antibody or a polyclonal antibody. The anti-GAS6 antibody may also be a commercially available antibody, and such a commercially available antibody can be purchased, for example, from R & D Systems, Santa Cruz Biotechnology, etc. The concentration of the anti-GAS6 antibody contained in a medium for culturing pluripotent stein cells is not particularly limited. It is preferably 1 ng/ml or more and 100 ng/ml or less, and more preferably 10 ng/ml or more and 100 ng/ml or less.

The type of the GAS6 receptor tyrosine kinase inhibitor used in the present invention is not particularly limited. The GAS6 receptor tyrosine kinase inhibitor used herein is preferably an inhibitor of receptor tyrosine kinases (TYRO3, AXL, and MER) of the TAM family. Specific examples of the GAS6 receptor tyrosine kinase inhibitor include: BMS777607 [N-(4-((2-amino-3-chloropyridin-4-yl)oxy)-3-fluorophenyl)-4-ethoxy-1-(4-fluorophenyl)-2-oxo-1,2-dihydropyridine-3-carboxamide]; R428 [1-(6,7-dihydro-5H-benzo[2,3]cyclohepta[2,4-d]pyridazin-3-yl)-3-N-[(7S)-7-pyrolidin-1-yl-6,7,8,9-tetrahydro-5H-benzo[7]annulen-3-yl]-1,2,4-triazole-3,5-diamine]; and UNC569 [1-((trans-4-aminocyclohexyl)methyl)-N-butyl-3-(4-fluorophenyl)-1H-pyrazolo[3,4-d]pyrimidin-6-amine].

In the case of using BMS777607, the concentration of the BMS777607 contained in a medium is generally 1 ng/ml or more and 100 ng/ml or less, and preferably 2 ng/ml or more and 20 ng/ml or less. In the case of using R428, the concentration of the R428 contained in a medium is generally 1 ng/ml or more and 500 ng/ml or less, and preferably 8 ng/ml or more and 80 ng/ml or less. In the case of using UNC569, the concentration of the UNC569 contained in a medium is generally 0.5 ng/ml or more and 100 ng/ml or less, and preferably 1 ng/ml or more and 10 ng/ml or less.

The culturing of pluripotent stem cells under conditions in which the action of GAS6 is inhibited is preferably a culturing of pluripotent stem cells in the presence of an anti-GAS6 antibody and/or a GAS6 receptor tyrosine kinase inhibitor.

When pluripotent stem cells are cultured under conditions in which the action of GAS6 is inhibited, an aspect in which the pluripotent stem cells are cultured in a medium, which does not comprise albumin, an aspect in which the cells are cultured in a medium, which does not comprise serum, and an aspect in which the cells are cultured in a medium containing GAS6 are preferable, and further, these aspects may also be combined with one another.

The present invention will be more specifically described in the following examples. However, these examples are not intended to limit the scope of the present invention.

EXAMPLES (1) Detection of Protein in Conditioned Serum-Free Medium

A conditioned medium (CM) was prepared from a serum-free medium, using mouse embryonic fibroblasts (MEF cells) that had been inactivated by mitomycin treatment. The mouse embryonic fibroblasts (MEF cells) that had been inactivated by the mitomycin treatment were inoculated at a cell density of approximately 500,000 cells/a dish with a diameter of 60 mm in a medium for MEF (DMEM medium containing 10% FBS). The cells were cultured for at least 16 hours, and thereafter, the resulting cells were washed with PBS(−), and then with an Essential 8 medium (Invitrogen) (hereinafter this serum-free medium is also referred to as an "E8 medium"). After that, the medium was replaced with a fresh serum-free medium of the same type.

After the medium had been replaced with a fresh one, the medium was incubated for 24 hours in a $CO_2$ incubator (37° C., 5% $CO_2$ concentration), and it was then recovered, thereby obtaining a conditioned medium.

An unconditioned serum-free medium and a conditioned serum-free medium were subjected to comparative analysis using an anti-cytokine antibody array. 100 μL of Blocking Buffer (included with a kit) was applied onto an array of RayBio® Mouse Cytokine Antibody array G-Series 2000 (RayBiotech), and it was then incubated at 25° C. for 30 minutes. Thereafter, 150 μL of each medium (dilution magnification: 1.5, approximately 155 μg relative to protein) was applied onto the array, and it was then incubated at 10° C. for 16 hours. Thereafter, the resultant was washed with Wash Buffer I (included with the kit, 25° C., 2 minutes×3 times, 25° C., 10 minutes×2 times), and then with Wash Buffer II (included with the kit, 25° C., 10 minutes×2 times). After completion of the washing operations, 70 μL of Biotin-Conjugated Antibody was applied onto the array, and it was then incubated at 25° C. for 2 hours. After that, the array was washed with Wash Buffer I (25° C., 2 minutes), and then with Wash Buffer II (25° C., 2 minutes×2 times). Thereafter, 70 μL of Fluorescent Dye-Conjugated Streptavidin was applied onto the array, and it was then incubated at 25° C. for 1.5 hours. The array was washed with Wash Buffer I (25° C., 2 minutes), Wash Buffer II (25° C., 2 minutes×2 times), Wash Buffer I (25° C., 10 minutes×2 times), and ultrapure water (25° C., 1 minute). The washed array was centrifuged at 1000 rpm at 25° C. for 3 minutes, and was then dried for 20 minutes under light-shielded conditions. Using an array scanner GenePix® 4400A (Molecular Devices, LLC), scanning was carried out, and then, using analysis software Array-Pro Analyzer Ver. 4.5 (Media Cybernetics, Inc.), the fluorescence intensity value in each spot was quantified from the obtained image.

As a result, decorin, matrix metalloproteinase-3 (MMP3), osteopontin (OPN), TWEAK R, insulin-like growth factor-binding protein 2 (IGFBP2), galectin 1 (LGALS1), insulin-like growth factor-1 (IGF-1), and a GAS6 protein were detected specifically in the conditioned serum-free medium.

(2) Cytokine Addition Test 1

(2-1) Case of Unconditioned Serum-Free Medium or Conditioned Serum-Free Medium

Human iPS cells (201B7) used in the experiment were obtained from iPS Academia Japan, Inc. Human iPS cells were prepared by carrying out a maintenance culture on a plastic culture dish, on which mouse embryonic fibroblasts inactivated by a mitomycin treatment were plated as feeder cells. A medium prepared by adding KNOCKOUT™ SR (final concentration: 20%), 0.1 mM NEAA (non-essential amino acids), 2 mM L-glutamine, 5 ng/ml human basic FGF and 0.1 mM 2-mercaptoethanol to D-MEM/F12 (Sigma D6421) was used. The cells were cultured at 37° C. in a $CO_2$ incubator. Subculture was carried out every 6 to 7 days, and using a dissociation solution (collagen solution), a colony of human iPS cells was removed from a feeder layer, and about 20 to 50 small masses were then obtained by a pipetting operation. The obtained small masses were plated on a fresh feeder cell layer. Human iPS cells, which had been subjected to a maintenance culture on feeder cells, were removed using a dissociation solution, and about 20 to 50 small masses were then obtained by a pipetting operation. The masses were centrifuged at 300 rpm for 5 minutes to recover iPS cells, and MEF was then removed by incubation of the cells on a gelatin-coated culture dish for 30 minutes. The resulting cells were divided into 4 portions, and the one portion was then inoculated on a culture dish coated with Matrigel (registered trademark) (BD). As a medium, a serum-free medium (E8 medium) that had not been conditioned with MEF was used, and it was compared with an E8 medium that had been conditioned with MEF.

The results regarding the comparison of proliferative ability are shown in Table 1. Moreover, the results obtained by adding individual factors to the medium, culturing the mixture for 2 days, and then staining the resultant with alkaline phosphatase, followed by observation, are shown in FIG. 1. It was found that the proliferative efficiency of human iPS cells was improved in the conditioned medium, in comparison to in the unconditioned medium.

(2-2)

A factor, namely, decorin, matrix metalloproteinase-3 (MMP3), osteopontin (OPN), TWEAK R, insulin-like growth factor-binding protein 2 (IGFBP2), galectin 1 (LGALS1), or insulin-like growth factor-1 (IGF-1), was added in a concentration of 2 ng/ml or 10 ng/ml to a serum-free medium (E8 medium), and the influence of each factor on the growth of human iPS cells was then examined, as in the case of (2-1) above.

The results regarding the comparison of proliferative ability are shown in Table 1, and the results obtained by staining the cells with alkaline phosphatase and then observing them are shown in FIG. 1 and FIG. 2. It was found that decorin, galectin 1 (LGALS1) and insulin-like growth factor-1 (IGF-1) have the effect of promoting the growth of human iPS cells. It has been reported that decorin can be used as a coating substrate for a culture substrate in the culture of human pluripotent stem cells (WO 9920741), and it has also been reported that galectin 1 promotes the growth of mouse ES cells (KR2010130677A). IGF-1 factors are added to a medium such as STEMPRO hESC SFM (manufactured by Life Technologies).

(2-3)

GAS6 was added in a concentration of 2 ng/ml or 100 ng/ml to a serum-free medium (E8 medium), and the influence of GAS6 on the growth of human iPS cells was then examined, as in the case of (2-1) above. The results regarding the comparison of proliferative ability are shown in Table 1, and the results obtained by staining the cells with alkaline phosphatase and then observing them are shown in FIG. 2. As a result, it could be confirmed that GAS6 has the effect of promoting the growth of human iPS cells.

(2-4)

All of GAS6, decorin, matrix metalloproteinase-3 (MMP3), osteopontin (OPN), TWEAK R, insulin-like growth factor-binding protein 2 (IGFBP2), galectin 1 (LGALS1), and insulin-like growth factor-1 (IGF-1) were added in each concentration of 2 ng/ml or 100 ng/ml to a serum-free medium (E8 medium), and the influence of these factors on the growth of human iPS cells was then examined, as in the case of (2-1) above. The results regarding the comparison of proliferative ability with respect to a medium to which only GAS6 was added are shown in Table 1, and the results obtained by staining the cells with alkaline phosphatase and then observing them are shown in FIG. 2. A higher effect of promoting the growth of human iPS cells was found in a medium to which all of the aforementioned 8 factors had been added, than in a medium to which only GAS6 had been added.

(3) Cytokine Addition Test 2

As media, the following media were used, and the influence thereof on the growth of human iPS cells was examined, as in the case of (2-1) above.

Serum-Free Medium that has not been Conditioned with MEF (E8 Medium);

The above-described E8 medium that has been conditioned with MEF (E8CM);

E8 medium, to which any one of decorin (100 ng/ml), matrix metalloproteinase-3 (MMP3) (2 ng/ml), GAS6 (2 ng/ml), osteopontin (OPN) (100 ng/ml), TWEAK R (2 ng/ml), insulin-like growth factor-binding protein 2 (IGFBP2) (2 ng/ml), galectin 1 (LGALS1) (2 ng/ml), insulin-like growth factor-1 (IGF-1) (100 ng/ml) and BA (100 ng/ml) has been added;

E8 medium, to which all of decorin (100 ng/ml), matrix metalloproteinase-3 (MMP3) (2 ng/ml), GAS6 (2 ng/ml), osteopontin (OPN) (100 ng/ml), TWEAK R (2 ng/ml), insulin-like growth factor-binding protein 2 (IGFBP2) (2 ng/l), galectin 1 (LGALS1) (2 ng/ml), and insulin-like growth factor-1 (IGF-1) (100 ng/ml) have been added (E8+8);

E8 medium conditioned with MEF, to which all of decorin (100 ng/ml), matrix metalloproteinase-3 (MMP3) (2 ng/ml), GAS6 (2 ng/ml), osteopontin (OPN) (100 ng/ml), TWEAK R (2 ng/ml), insulin-like growth factor-binding protein 2 (IGFBP2) (2 ng/ml), galectin 1 (LGALS1) (2 ng/ml), and insulin-like growth factor-1 (IGF-1) (100 ng/ml) have been added (E8CM+8);

E8 medium, to which decorin (100 ng/ml), GAS6 (2 ng/ml), osteopontin (OPN) (100 ng/ml), TWEAK R (2 ng/ml), insulin-like growth factor-binding protein 2 (IGFBP2) (2 ng/ml), galectin 1 (LGALS1) (2 ng/ml), and insulin-like growth factor-1 (IGF-1) (100 ng/ml) have been added (E8+8−MMP3); and E8 medium, to which decorin (100 ng/ml), matrix metalloproteinase-3 (MMP3) (2 ng/ml), GAS6 (2 ng/ml), TWEAK R (2 ng/ml), insulin-like growth factor-binding protein 2 (IGFBP2) (2 ng/ml), galectin 1 (LGALS1) (2 ng/ml), and insulin-like growth factor-1 (IGF-1) (100 ng/ml) have been added (E8+8−OPN).

The results regarding the comparison of the proliferative ability of cells are shown in Table 1. In addition, the cells were stained with alkaline phosphatase and the number of cells was then counted, as described in (2-1) above. The number of cells in the case of using an E8 medium was defined as 1 and the results regarding the ratio of the number of cells in the case of using another medium to that in the case of using the E8 medium are shown in FIG. 3.

(4) Cytokine Addition Test 3

As media, the following media were used, and the influence thereof on the growth of human iPS cells was examined, as in the case of (2-1) above.

Serum-Free Medium that has not been Conditioned with MEF (E8 Medium);

The above-described E8 medium that has been conditioned with MEF (E8CM);

E8 medium, to which any one of decorin (100 ng/ml), GAS6 (100 ng/ml), osteopontin (OPN) (100 ng/ml), galectin 1 (LGALS1) (100 ng/ml), insulin-like growth factor-1 (IGF-1) (100 ng/ml) and BSA (100 ng/ml) has been added; and E8 medium, to which all of decorin (100 ng/ml), matrix metalloproteinase-3 (MMP3) (100 ng/ml), GAS6 (100 ng/ml), osteopontin (OPN) (100 ng/ml), TWEAK R (100 ng/ml), insulin-like growth factor-binding protein 2 (IGFBP2) (100 ng/ml), galectin 1 (LGALS1) (100 ng/ml) and insulin-like growth factor-1 (IGF-1) (100 ng/ml) have been added.

The results regarding the comparison of the proliferative ability of cells are shown in Table 1. The results obtained by staining the cells with alkaline phosphatase and observing them are shown in FIG. 4. It was found that the proliferative efficiency of human iPS cells was improved in a medium to which GAS6 had been added. In addition, the cells were stained with alkaline phosphatase, and the number of cells was then counted. The number of cells in the case of using an E8 medium was defined as 100, and the results regarding the ratio of the number of cells in the case of using another medium to that in the case of using the E8 medium are shown in FIG. 5.

TABLE 1

| | Cytokine addition test 1 | | Cytokine addition test 2 | | Cytokine addition test 3 |
|---|---|---|---|---|---|
| Concentration (ng/ml) | 2 | 100 | 2 | 100 | 100 |
| Without conditioning | − | | − | | − |
| With conditioning | ++ | | ++ | | + |
| Decorin | + | ++ | | + | + |
| MMP3 | + | + | + | | |
| OPN | + | + | | ± | ± |
| TWEAK R | + | + | + | | |
| IGFBP2 | ++ | ++ | + | | |
| Galectin 1 | ++ | ++ | + | | + |
| IGF-1 | ++ | ++ | | + | + |
| GAS6 | + | + | + | | + |
| Total (8 factors) | +++ | +++ | + | + | + |

(5) As to Matrigel

Using a culture dish that had not been coated with Matrigel (registered trademark) (BD), instead of using a culture dish that had been coated with Matrigel (registered trademark) (BD), and using an unconditioned serum-free medium or a conditioned serum-free medium, as in the case of (2-1) above, a comparison was made in terms of the proliferative ability of human iPS cells. The results obtained by staining the cells with alkaline phosphatase and then observing them are shown in FIG. 6. In the case of using a conditioned medium, the cells could proliferate even in the case of using a culture dish that had not coated with Matrigel.

(6) As to Anti-GAS6 Antibody

Using a culture dish that had been coated with Matrigel (registered trademark) (BD), 100 ng/ml anti-GAS6 antibody (R & D Systems) was added to a serum-free medium (E8 medium) conditioned with MEF, and the influence of the antibody on the growth of human iPS cells was then examined, as in the case of (2-1) above. The cells were stained with alkaline phosphatase, and the number of cells was then counted. The number of cells in the case of using a medium conditioned with MEF was defined as 100, and the results regarding the ratio of the number of cells in the case of using another medium to that in the case of using the medium conditioned with MEF are shown in FIG. 7. By adding the anti-GAS6 antibody, the proliferative ability of cells in the medium conditioned with MEF was reduced.

(7) As to Anti-GAS6 Antibody and GAS6 Receptor Tyrosine Kinase Inhibitor

Using a culture dish that had been coated with Matrigel (registered trademark) (BD), 10 ng/ml or 100 ng/ml anti-GAS6 antibody (R & D Systems), or various types of GAS6 receptor tyrosine kinase inhibitors, namely, BMS777607 (Santa Cruz Biotechnology) (2 ng/ml or 20 ng/ml), R428 (Synkinase) (8 ng/ml or 80 ng/ml), and UNC569 (Calbiochem) (1 ng/ml or 10 ng/ml) were each added to a serum-free medium conditioned with MEF (E8 medium), and the influence thereof on the growth of human iPS cells was then examined, as in the case of (2-1) above. These factors were each dissolved in DMSO, and the obtained solution was then subjected to a filter sterilization treatment using a 0.22-μm filter. The thus treated solution was added to the medium in an amount of 1/1000 the amount of the medium. The cells were stained with alkaline phosphatase, and the number of cells was then counted. The number of cells in the case of using a medium conditioned with MEF was defined as 100, and the results regarding the ratio of the number of cells in the case of using another medium to that in the case of using the medium conditioned with MEF are shown in FIG. 8. By adding an anti-GAS6 antibody or various types of GAS6 receptor tyrosine kinase inhibitors, the proliferative ability of the cells in the medium conditioned with MEF was reduced.

The invention claimed is:

1. A method for culturing cells, said method comprising:
culturing cells using a cell culture medium, wherein the cell culture medium comprises growth arrest-specific 6 (GAS6), a basal medium, and at least one selected from the group consisting of decorin, matrix metalloproteinase-3 (MMP3), osteopontin (OPN), TNF-related weak inducer of apoptosis receptor (TWEAK R), insulin-like growth factor-binding protein 2 (IGFBP2), galectin 1 (LGALS1), and insulin-like growth factor-1 (IGF-1),
wherein the cell culture medium does not comprise serum, and the concentration of the GAS6 contained in the cell culture medium is between 2 ng/ml and 100 ng/ml, and
wherein the cells are cultured on a culture substrate having a surface that has not been coated with an extracellular matrix.

2. The culture method according to claim 1, wherein the culture cell culture medium is a liquid cell culture medium.

3. A method for culturing cells, said method comprising:
culturing cells using a cell culture medium, wherein the cell culture medium comprises growth arrest-specific 6 (GAS6), a basal medium, and at least one selected from the group consisting of decorin, matrix metalloproteinase-3 (MMP3), osteopontin (OPN), TNF-related weak inducer of apoptosis receptor (TWEAK R), insulin-like growth factor-binding protein 2 (IGFBP2), galectin 1 (LGALS1), and insulin-like growth factor-1 (IGF-1),
wherein the cell culture medium does not comprise serum, and the concentration of the GAS6 contained in the cell culture medium is between 2 ng/ml and 100 ng/ml, and
wherein the cells that are cultured are iPS cells (induced pluripotent stem cells).

4. The culture method according to claim 3, wherein the cells are cultured on a culture substrate coated with an extracellular matrix.

5. A method for culturing cells, which comprises culturing cells using a cell culture medium which comprises growth arrest-specific6 (GAS6), decorin, matrix metalloproteinase-3 (MMP3), osteopontin (OPN), TNF-related weak inducer of apoptosis receptor (TWEAK R), insulin-like growth factor-binding protein 2 (IGFBP2), galectin 1 (LGALS1), and insulin-like growth factor-1 (GF-1), does not comprise serum, and is not conditioned with MEF.

6. The culturing method according to claim 5, wherein the cells that are cultured are iPS cells (induced pluripotent stem cells).

7. The method according to claim 6, wherein said iPS cells are not exposed during culturing to either animal cells or a culture solution conditioned with said animal cells.

* * * * *